(12) United States Patent
Lemoine et al.

(10) Patent No.: US 10,675,060 B2
(45) Date of Patent: Jun. 9, 2020

(54) CRANIAL BURR HOLE COVER

(71) Applicants: Pat Lemoine, Jacksonville, FL (US); Shawn Burke, Jacksonville, FL (US)

(72) Inventors: Pat Lemoine, Jacksonville, FL (US); Shawn Burke, Jacksonville, FL (US)

(73) Assignee: KLS-MARTIN, L.P., Jacksonville, FL (US)

( * ) Notice: Subject to any disclaimer, the term of this patent is extended or adjusted under 35 U.S.C. 154(b) by 34 days.

(21) Appl. No.: 16/038,928

(22) Filed: Jul. 18, 2018

(65) Prior Publication Data
US 2018/0317985 A1 Nov. 8, 2018

Related U.S. Application Data

(63) Continuation-in-part of application No. 14/677,515, filed on Apr. 2, 2015, now abandoned.

(60) Provisional application No. 61/974,130, filed on Apr. 2, 2014.

(51) Int. Cl.
*A61B 17/68* (2006.01)
*A61B 17/80* (2006.01)
*A61B 17/88* (2006.01)

(52) U.S. Cl.
CPC ........ *A61B 17/688* (2013.01); *A61B 17/8085* (2013.01); *A61B 17/8872* (2013.01)

(58) Field of Classification Search
CPC ....... A61B 17/68; A61B 17/688; A61B 17/80; A61B 17/8061; A61B 17/808; A61B 17/8085; A61B 17/88; A61B 17/8872; A61B 2090/103
See application file for complete search history.

(56) References Cited

U.S. PATENT DOCUMENTS

| | | | | |
|---|---|---|---|---|
| 6,022,351 A | * | 2/2000 | Bremer | A61B 17/688 606/324 |
| 6,126,663 A | * | 10/2000 | Hair | A61B 17/688 606/324 |
| 6,379,363 B1 | * | 4/2002 | Herrington | A61B 17/688 606/104 |
| 6,685,707 B2 | * | 2/2004 | Roman | A61B 17/688 606/213 |

(Continued)

FOREIGN PATENT DOCUMENTS

| | | | | |
|---|---|---|---|---|
| JP | 05220174 A | * | 8/1993 | ........... A61B 17/688 |
| JP | 2003180706 A | * | 7/2003 | ........... A61B 17/688 |

*Primary Examiner* — Eric S Gibson
(74) *Attorney, Agent, or Firm* — Thomas C. Saitta

(57) ABSTRACT

A method of affixing a cranial burr hole cover comprising an elongated internal bracing member, a locking external cover member joined by one or more connecting members, and a locking mechanism, whereby the interior bracing member is tilted and one end is inserted through the burr hole and under the skull. The internal bracing member is then moved laterally relative to the burr hole to allow the opposite end of the internal bracing member to clear the opposite edge of the burr hole. The internal bracing member is then centered beneath the burr hole. The external cover member is now moved distally toward the skull to cover the burr hole. The locking mechanism secures the cover in place on the skull and the connecting members extending from the cover member are cut flush with the cover member.

7 Claims, 9 Drawing Sheets

(56) References Cited

U.S. PATENT DOCUMENTS

| | | | |
|---|---|---|---|
| 6,921,401 B2* | 7/2005 | Lerch | A61B 17/688 606/232 |
| 7,833,253 B2* | 11/2010 | Ralph | A61B 17/688 403/397 |
| 8,241,342 B2* | 8/2012 | Kirschman | A61B 17/688 606/324 |
| 9,034,020 B2* | 5/2015 | Knopfle | A61B 17/688 606/282 |
| 9,149,297 B2* | 10/2015 | Kirschman | A61B 17/688 |
| 9,265,530 B2* | 2/2016 | Llas Vargas | A61B 17/8061 |
| 9,433,438 B2* | 9/2016 | Memmolo | A61B 17/688 |
| 9,770,264 B2* | 9/2017 | Carvani | A61B 17/8872 |
| 2002/0016593 A1* | 2/2002 | Hearn | A61B 17/688 606/916 |
| 2002/0062128 A1* | 5/2002 | Amis | A61B 17/688 606/916 |
| 2002/0156475 A1* | 10/2002 | Lerch | A61B 17/688 606/70 |
| 2002/0169455 A1* | 11/2002 | Bannerman | A61B 17/688 606/99 |
| 2003/0036760 A1* | 2/2003 | Yeh | A61B 17/688 606/71 |
| 2004/0034375 A1* | 2/2004 | Ruiz | A61B 17/688 606/151 |
| 2004/0102779 A1* | 5/2004 | Nesper | A61B 17/688 606/324 |
| 2004/0116961 A1* | 6/2004 | Nesper | A61B 17/688 606/216 |
| 2004/0127908 A1* | 7/2004 | Roman | A61B 17/688 606/916 |
| 2006/0259040 A1* | 11/2006 | Wellisz | A61B 17/688 606/916 |
| 2008/0275511 A1* | 11/2008 | Weinacker | A61B 17/688 606/324 |
| 2008/0281339 A1* | 11/2008 | Kirschman | A61B 17/688 606/151 |
| 2009/0076617 A1* | 3/2009 | Ralph et al. | A61B 17/688 623/17.19 |
| 2010/0305619 A1* | 12/2010 | Knopfle | A61B 17/688 606/282 |
| 2012/0290018 A1* | 11/2012 | Kirschman | A61B 17/688 606/324 |
| 2013/0110181 A1* | 5/2013 | Piotrowski | A61B 17/688 606/324 |
| 2013/0282011 A1* | 10/2013 | Brogan | A61B 17/688 606/75 |
| 2014/0072386 A1* | 3/2014 | Baugh, Sr. | F16B 19/00 411/337 |
| 2014/0135852 A1* | 5/2014 | Memmolo | A61B 17/688 606/324 |
| 2014/0171944 A1* | 6/2014 | Llas Vargas | A61B 17/8061 606/70 |
| 2015/0282840 A1* | 10/2015 | Lemoine | A61B 17/688 606/213 |
| 2017/0189069 A1* | 7/2017 | Carvani | A61B 17/8872 |
| 2018/0317969 A1* | 11/2018 | Lemoine | A61B 17/688 |
| 2018/0317985 A1* | 11/2018 | Lemoine | A61B 17/8085 |

* cited by examiner

CRANIAL BURR HOLE COVER

BACKGROUND OF THE INVENTION

This application relates generally to the field of cranial burr hole covers, and more particularly relates to such covers structured in the nature of clamps wherein a member positioned interiorly on the skull and a member positioned exteriorly on the skull are locked together to cover the burr hole.

In cranial surgery it is often necessary to cut burr holes through the skull to directly access a portion of the brain or to provide an access means for the insertion of saws or other cutting implements in order to remove a larger section of the skull, often referred to as a flap. In order to secure the flap to the skull once the flap is replaced, it is known to provide craniotomy pins, such as shown in U.S. Pat. No. 5,549,620 to Bremer. The pins comprise a large external head possessing lateral dimensions greater than the width of the gap between the flap and skull, a post or shaft member sized to be able to reside within the gap, and an internal locking member. The internal locking member is generally rectangular in shape and is sized to have a longitudinal dimension greater than the width of the gap and a lateral dimension smaller than the width of the gap. With this configuration, the longitudinal dimension of the internal locking member of the craniotomy pin is aligned with the gap such that the internal locking member can be pushed into the gap. The pin is then rotated so that the longitudinal dimension is now perpendicular to the gap, the ends of the internal locking member precluding removal of the pin without rotation of the pin. The craniotomy pin of this configuration is not designed for use in covering the burr holes disposed at the ends or midportion of the gaps, since the longitudinal dimension of the internal locking member would need to greater than the diameter of the burr hole, which is several times greater than the width of the gap. This would make rotation of the pin difficult and possibly cause damage to the underlying tissue. The craniotomy pin of this configuration is not suitable in any way for covering isolated burr holes where no flap has been removed and replaced, since there is no gap for insertion and then rotation of the internal locking member. Furthermore, the fixed separation distance between the external head and the internal locking member does not allow adjustment of the clamping pressure, i.e., movement of the external head toward the internal locking member.

It is known to provide clamping covers, i.e., adjustable covers that can be tightened onto the skull or bone flap, for the both gaps and burr holes, wherein the covers comprise a disk-shaped internal member and a disk-shaped external member held together by a connecting member provided with a locking mechanism, such as a ratchet system or screw threading. For use with burr holes, the diameter of the internal and external disk-shaped members must be greater than the diameter of the burr hole. This structure is suitable for use in circumstances where a flap portion of the skull has been removed between burr holes, since the internal disk-shaped members can be laterally positioned on the interior side of the skull prior to replacement of the skull. However, such covers cannot be utilized to cover an isolated burr hole, since the required size for the internal disk-shaped member prevents it from being inserted directly through the burr hole. An example of such a clamping cover is sold under the brand CRANIAL LOOP by KLS Martin Group.

Other cranial burr hole covers suitably structured to cover an isolated burr hole are shown in U.S. Pat. No. 6,126,663 to Hair and in U.S. Pat. No. 8,241,342 to Kirschman. The Hair device utilizes a plurality of leg-like connecting members extending from the external cover, with each connecting member terminating in an outwardly extending foot-like structure. In the neutral position the leg-like connecting members bend inward and can be inserted into the burr hole. A threaded spreading post is then driven into an axial opening to drive the foot-like structures radially outward to be positioned on the inside of the skull. This device is not depth-adjustable, as the distance between the foot-like members and the external cover is fixed. The structure of the device also requires excessive time to place each burr hole cover.

The Kirschman device comprises a pair of generally parallel connecting members extending through a disk-shaped cover member. Each connecting member has an outwardly extending tab member. The connecting members are flexed together to reduce the radial extension of the tab members for insertion through the burr hole. Once inserted the proper distance, the tab members are pressed outward to position them on the inside of the skull. The connecting members are provided with a ratchet surface that cooperates with slots in the external cover, such that the cover member can be pressed downward onto the skull to secure the device to the skull and cover the isolated burr hole. The portions of the connecting members extending above the external cover are then removed. Because the tab members are structured to flex inwardly, proper placement of the device requires the surgeon to maintain the spread of the tabs after insertion using an instrument or a finger while simultaneously lowering the external cover into the clamped and secured position.

It is an object of this invention to provide an adjustable cranial burr hole cover suitable for use with single, isolated burr holes, and a method of covering an isolated burr hole using this cover, wherein the problems inherent known burr hole covers are overcome.

SUMMARY OF THE INVENTION

The cranial burr hole cover is an adjustable clamping cover comprising a single, elongated, substantially or fully planar, internal bracing member and an external locking cover member joined by one or more connecting members, the external locking cover having a disk-shaped configuration which in application is chosen to have a diameter greater than the diameter of the isolated burr hole to be covered. The connecting members initially extend through and beyond the external cover member both distally and proximally prior to positioning the cover clamp in the burr hole. The external cover member is structured such that it may be moved distally along the connecting members toward the internal bracing member. A locking mechanism, such as a ratchet mechanism, is provided that precludes movement of the external cover member relative to the connecting members in the proximal direction once the cover is secured onto the skull.

The single, elongated, substantially or fully planar, internal bracing member is configured to have a longitudinal dimension and a maximum width dimension, the maximum width dimension being significantly smaller than the longitudinal dimension. For a given circular burr hole, the internal bracing member will be sized such that the longitudinal dimension or length of the internal bracing member is greater than the diameter of the burr hole and the maximum width dimension or width is less than the diameter of the burr hole. In this manner the internal bracing member may be generally rectangular or elliptical in configuration. The one or more connecting members are preferably mounted to the internal bracing member at the longitudinal midpoint or midline of the internal bracing member such that a clearance distance is defined between one of the longitudinal edges and the opposite side of the farthest connecting member, the clearance distance being shorter than the diameter of the burr hole. For embodiments having two connecting members, the distal ends of the connecting members are joined to the internal bracing member in a fixed manner such that the distance between the distal ends of the connecting members is not variable.

With this structure the interior bracing member of the burr hole cover may be inserted through the circular burr hole by holding the connector members and tilting the internal bracing member such that a longitudinal end of the internal bracing member is able to be inserted into the hole and under the skull. The internal bracing member is then moved laterally relative to the burr hole to bring the connecting members close enough to the edge of the burr hole to allow the opposite end of the internal bracing member to clear the opposite edge of the burr hole. The internal bracing member is then leveled relative to the skull and moved laterally to center the internal bracing member beneath the burr hole with both longitudinal ends now positioned beneath the skull. The external cover member is now moved distally along the connecting members toward the skull and the internal bracing member to cover the burr hole. The planar or substantially planar configuration of the internal bracing member minimizes damage to internal tissue located adjacent the burr hole during the positioning steps. The locking mechanism secures the cover in place on the skull and the connecting members extending from the cover member are cut flush with the cover member.

Alternatively expressed, the invention is a method of covering an isolated, circular burr hole in a skull comprising the steps of measuring the diameter of a burr hole to be covered; providing a cranial burr hole cover device comprising a single, elongated, internal bracing member, a disk-shaped, external cover member having a diameter, one or more connecting members joining said external cover member to said internal bracing member, and a locking mechanism whereby movement of said external cover member along said connecting members in the distal direction is allowed and movement of said external cover member in the proximal direction along said connecting members is precluded; said internal bracing member being substantially or fully planar and having a longitudinal dimension, a longitudinal midpoint or midline, and a maximum width dimension, said longitudinal dimension being greater than said maximum width dimension, such that said internal bracing member comprises a pair of longitudinal ends; said one or more connecting members joined to said internal bracing member at said midpoint or midline, whereby a clearance distance is defined extending from one of said longitudinal ends to the opposite side of said one or more connecting members; choosing said cranial burr hole cover device such that the diameter of said external cover member is greater than the diameter of the burr hole, such that said longitudinal dimension of said internal bracing member is greater than the diameter of the burr hole and said maximum width dimension of said internal bracing member is smaller than the diameter of the burr hole, and such that said clearance distance is smaller than the diameter of the burr hole; inserting one of said longitudinal ends of said internal bracing member, at an angle between perpendicular and parallel to the surface of the skull at the burr hole, through the burr hole and under the skull adjacent the burr hole; moving said internal bracing member laterally and inserting and leveling the other of said longitudinal ends of said internal bracing member through the burr hole, then centering said internal bracing member relative to the burr hole such that both said longitudinal ends and said entire internal bracing member are positioned on a distal side of the skull and burr hole; securing said internal bracing member and said external cover member to the skull by moving said external cover member distally along said connecting members toward said burr hole; and removing portions of said connecting members that are extending proximally from said external cover member.

Furthermore, such method wherein said step of providing a cranial burr hole cover device further comprises providing a cranial burr hole cover device having two connecting members with distal ends, the distal ends of said two connecting members being joined to said internal bracing member in fixed manner such that the distance between said distal ends is not variable; wherein said connecting members comprise a looped handle, and further comprising the step of grasping said looped handle with one hand or finger prior to said step of moving said external cover member distally along said connecting members toward said burr hole; wherein said burr hole cover device further comprises an actuator member mounted onto said one or more connecting members, and wherein said step of moving said external cover member distally along said connecting members toward said burr hole is accomplished by pressing against said actuator member; wherein said portions of said connecting members that are extending proximally from said external cover member are removed by cutting; and/or wherein said portions of said connecting members that are extending proximally from said external cover member are removed by breaking.

Additionally or alternatively, the invention is a cranial burr hole cover device comprising a single, elongated, planar, internal bracing member, said internal bracing member having a longitudinal dimension, a maximum width dimension, a longitudinal midpoint and lateral sides, said longitudinal dimension being greater than said width dimension, such that said internal bracing member comprises a pair of longitudinal ends; a disk-shaped, external cover member having a diameter greater than said maximum width dimension of said internal bracing member; one or more connecting members joining said external cover member to said internal bracing member, said connecting members being mounted to said internal cover member at said longitudinal midpoint or midline and adjacent said lateral sides in a fixed relationship; and a locking mechanism whereby movement of said external cover member along said connecting members in the distal direction is allowed and movement of said external cover member in the proximal direction along said connecting members is precluded. Furthermore, the invention may comprise the device wherein said locking mechanism comprises a ratchet mechanism; wherein said connecting members comprise bands and said locking mechanism comprises the combination of slots in said external cover member and teeth disposed on said bands; said connecting members further comprising a looped handle; and/or further comprising an actuator member disposed on said connecting members.

DETAILED DESCRIPTION OF THE INVENTION

Figure 1:
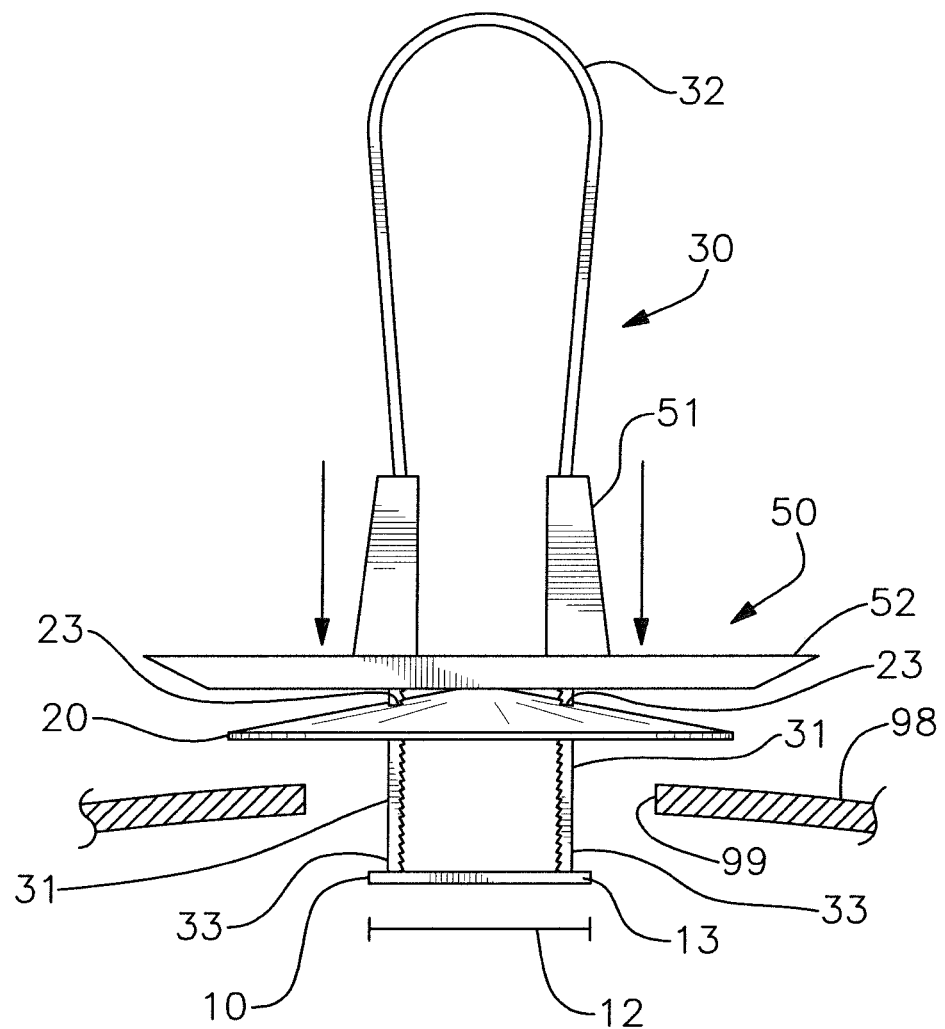
FIG. 1 is a view of an embodiment of the cranial burr hole cover invention showing an end view of the internal bracing member relative to a burr hole.
Figure 2:
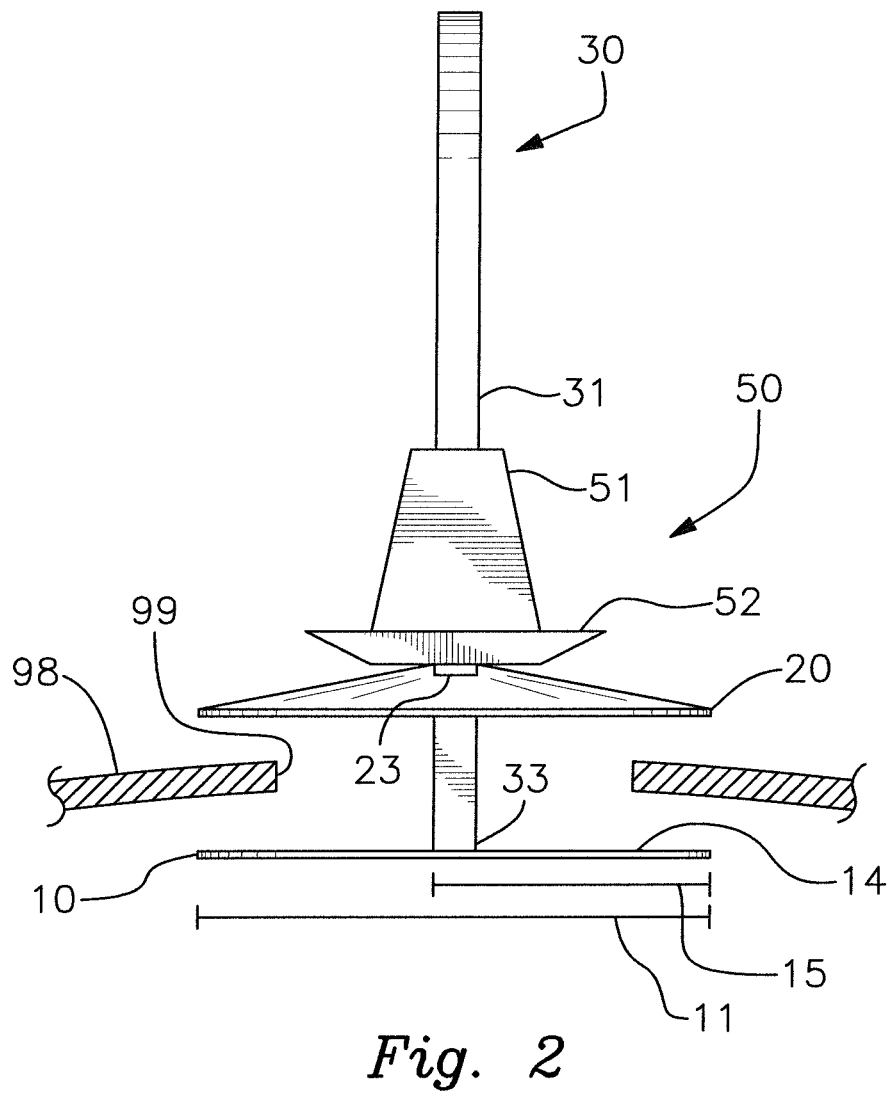
FIG. 2 is a view of the embodiment of FIG. 1 showing a side view of the internal bracing member.

With reference to the drawings, embodiments of the device and method will now be described. The illustrated embodiments of the cranial burr hole cover and methodology are not intended to be limiting. As used herein, the terms "proximal", "external" or similar terminology shall be taken to refer to the direction away from the skull when the device is being affixed and in use, and the terms "distal", "internal" or similar terminology shall be taken to refer to the direction toward and into the skull when the device is being affixed and in use.

The cranial burr hole cover device is a clamping cover comprising an internal bracing member 10 and a locking external cover member 20 joined by one or more connecting members 30, preferably two connecting members 30, the external cover member 20 preferably having a disk-shaped configuration which in application is chosen to have a diameter greater than the diameter of the burr hole 99 to be covered. The connecting members 30 initially extend through and beyond the external cover member 20 prior to positioning the clamping cover in the burr hole 99. The external cover member 20 is structured such that it may be moved distally along the connecting members 30 toward the internal bracing member. A locking mechanism 40, such as a ratchet mechanism of known type in the art, is provided that allows movement of the external cover member 20 relative to the connecting members 30 in the distal direction in order to affix the device to a skull 98, but precludes movement of the external cover member 20 relative to the connecting members 30 in the proximal direction once the clamping cover is secured onto the skull 98.

The external cover member 20 is preferably slightly concave so as to better approximate the curvature of the skull 98 when positioned across the burr hole 99 and is preferably composed of a slightly flexible material so as to flatten when secured. The periphery of the external cover 20 may be relatively circular or may be provided with notches 21 and projecting members 22 to increase flexibility, as shown in the embodiment of FIGS. 6-10. One or more slots 23 are provided for passage of the connecting members 30, such that the external cover member 20 is mounted onto the connecting members 20.

The internal bracing member 10 is a single, elongated, substantially or fully planar, member, formed of a relatively strong material, preferably a slightly flexible polymer material to better conform to the interior configuration of the skull 98, and is configured to have a longitudinal dimension or length 11 and a maximum width dimension or width 12, i.e., the widest portion of the internal bracing member 10, the width dimension 12 being significantly smaller than the longitudinal dimension 11. For a given circular burr hole 99, the cover to be applied is chosen such that the longitudinal dimension 11 of the internal bracing member 10 is greater than the diameter of the burr hole 99 and the width dimension 12 is less than the diameter of the burr hole 99. In this manner the internal bracing member 10 may be generally rectangular, elliptical, "dog-bone" shaped with a pair of opposing lobes, or of a similar periphery in configuration, comprising a pair of relatively short opposing longitudinal ends 13 and a pair of relatively long opposing lateral sides 14. Lateral sides 14 may be straight, curved inwardly, curved outwardly or of similar variations.

The one or more connecting members 30 are mounted to the internal bracing member 10 generally at the midpoint or midline with regard to the longitudinal dimension 11 such that a clearance distance 15 is defined between at least one of the longitudinal ends 13 and the opposite side of the connecting members 30, the clearance distance 15 being shorter than the diameter of the burr hole 99.

In the embodiments as shown in the drawings, the connecting members 30 may comprise a looped band 31 having two distal ends 33 secured to the internal bracing member 10 on or adjacent the lateral sides. The proximal portion of the looped band 31 may be widened to create a wider surface for easier handling. For embodiments having two connecting members 30, whether looped or independent, the distal ends 33 of the connecting members 30 are joined to the internal bracing member 10 in a fixed manner such that the distance between the distal ends 33 of the connecting members 30 is not variable, the internal bracing member 10 being a single or unitary body. Other configurations or structures for the connecting members 30, such as posts, columns, shafts, etc., may be utilized. Although not shown, the connecting member 30 could comprise a single member extending from the internal bracing member 10. The connecting members 30 are composed of a material that is easily cut or broken, such as a soft metal or a polymer material.

Figure 3:
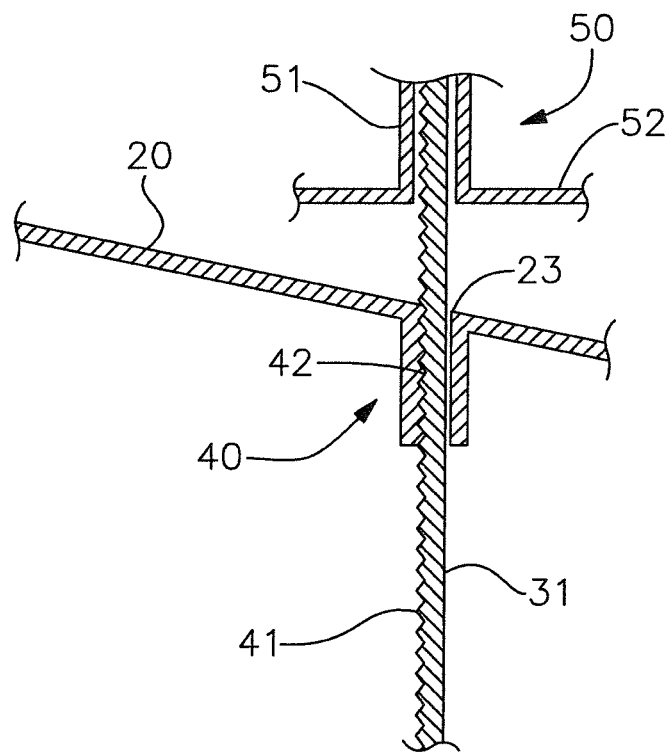
FIG. 3 is a partial view of the embodiment of FIG. 1 showing the locking mechanism between the external cover member and the connecting member and a portion of the actuator member.
Figure 5:
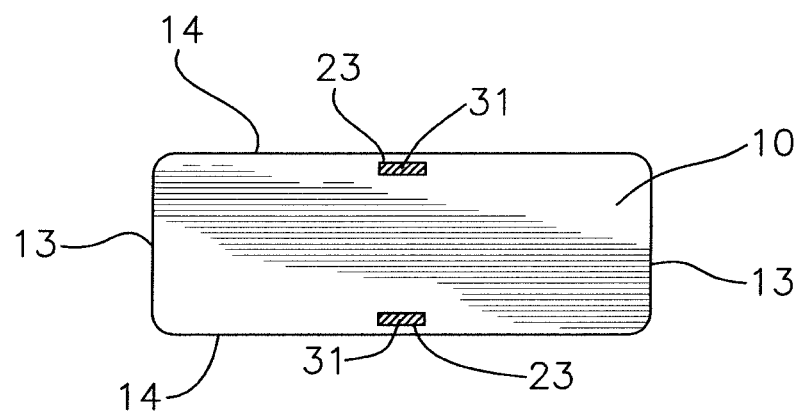
FIG. 5 is a top view of the internal bracing member showing the positioning of the connecting members of the embodiment of FIG. 1.
Figure 4:
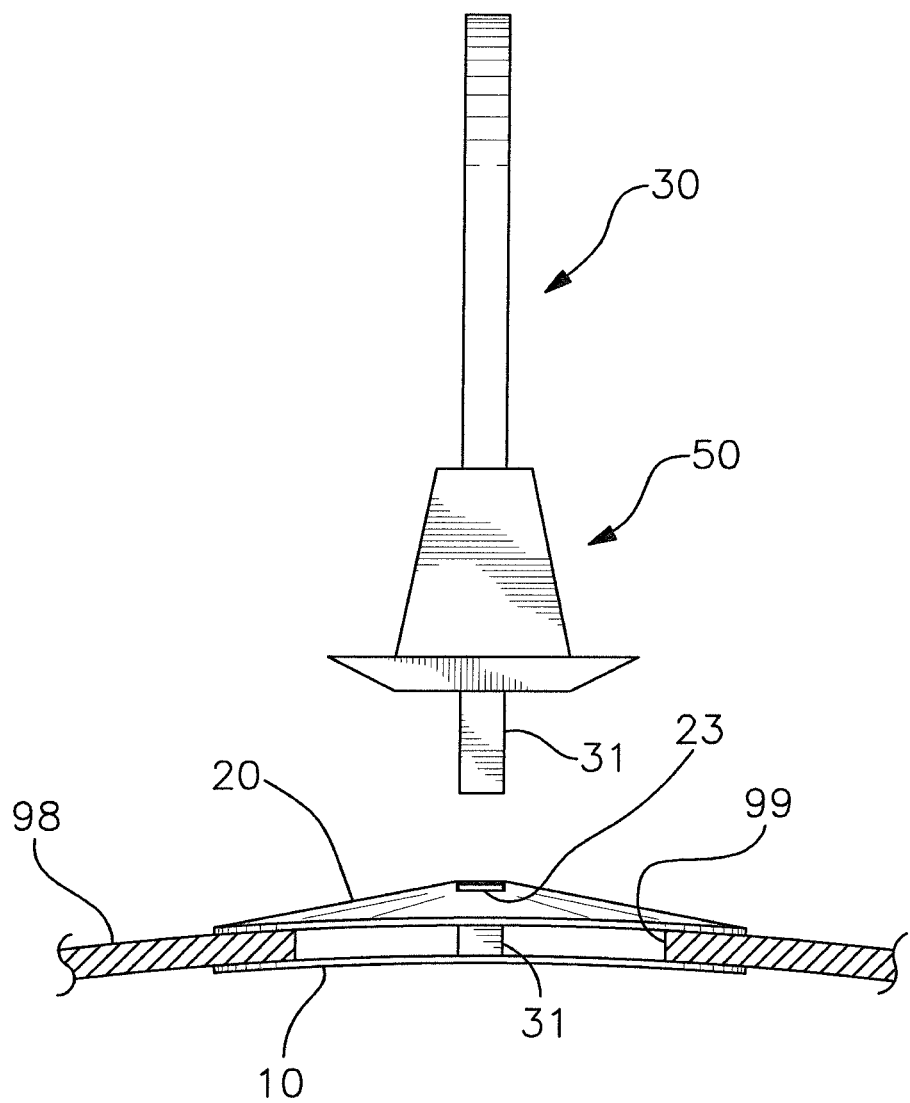
FIG. 4 is a view similar to FIG. 2 showing the external cover member clamped onto the skull to cover the burr hole and the excess connector members separated from the external cover member.
Figure 6:
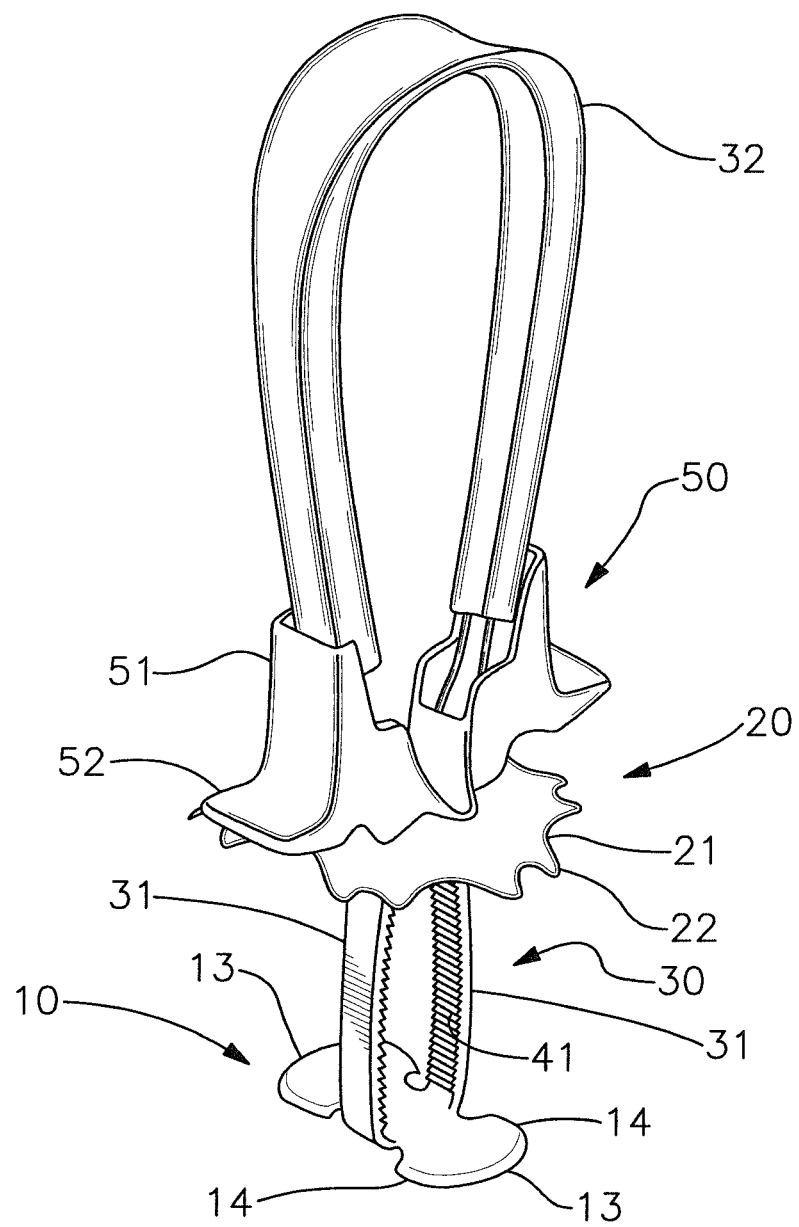
FIG. 6 is a view of an alternative embodiment of the cranial burr hole cover invention.

The locking mechanism 40 is a structural combination of elements that allows uni-directional movement of external cover member 20 along the connecting members 30 in the distal direction, i.e., towards the internal bracing member 10. For example, the locking member 40 may comprise a ratchet mechanism of known structure comprising ridges or teeth 41 disposed on the connecting members 30 which cooperate with locking shoulders or catches 42 mounted within the slots 23 of the external cover member 20, as shown in FIG. 3, to preclude movement in the proximal direction. Alternatively, slots 23 that do not extend beyond the body of the external cover member 20 may serve as the catches 42 for the teeth 41 disposed on the connecting members 30.

The clamping cover device may be provided with an actuator member 50 mounted onto the connecting members 30 to more easily enable force to be applied to the external cover member 20 to force it toward the internal bracing member 10. As shown, the actuator member 50 may comprise slotted housing 51 with a pair of lateral flanges 52, whereby the surgeon may push the actuator member 50 distally with the tips of the thumb and a finger while holding the looped handle 32 of the connecting members 30 with the other hand. The actuator member 50 is structured to easily move in either direction on the connector members 30.

Figure 7:
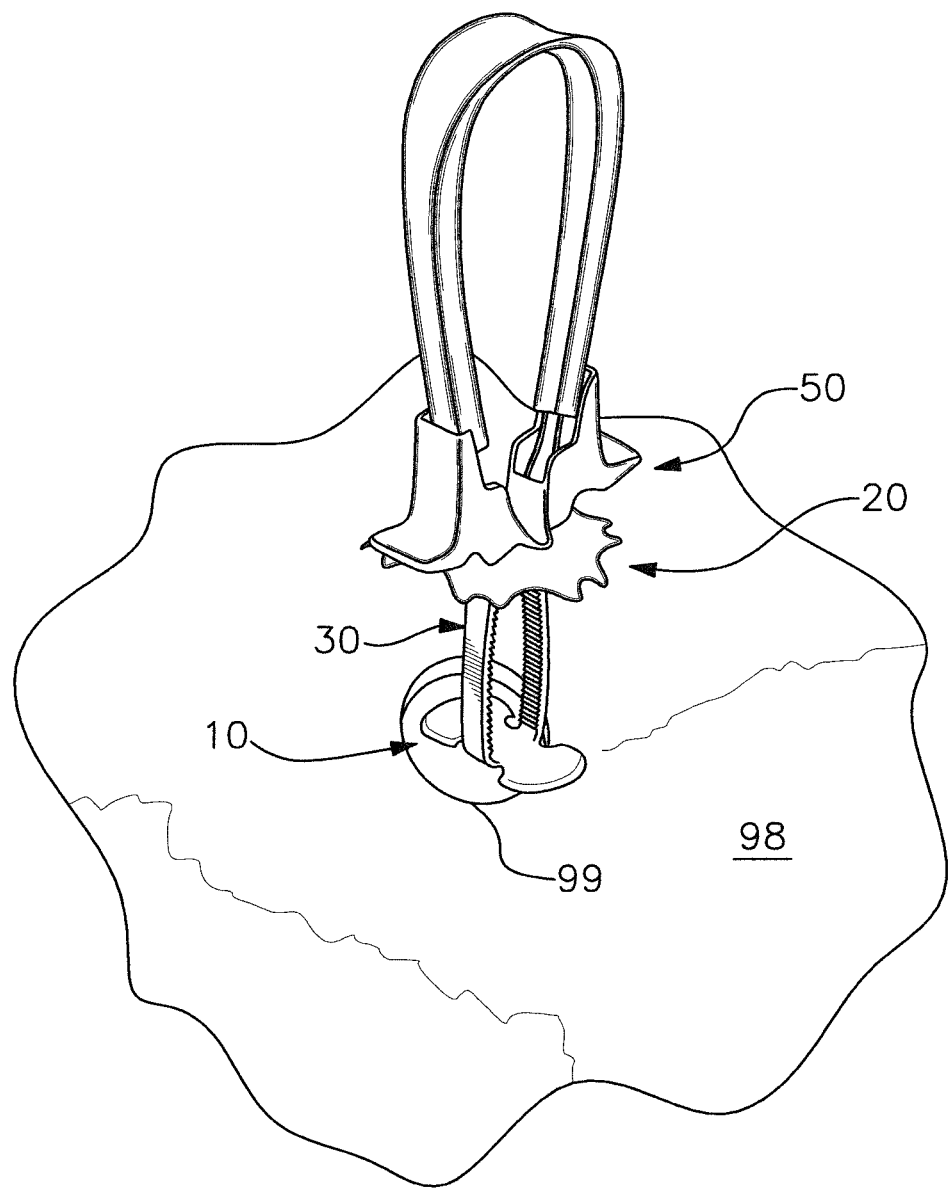
FIG. 7 illustrates the method of inserting the internal bracing member of the embodiment of FIG. 6 into an isolated burr hole by tilting the internal bracing member.
Figure 8:
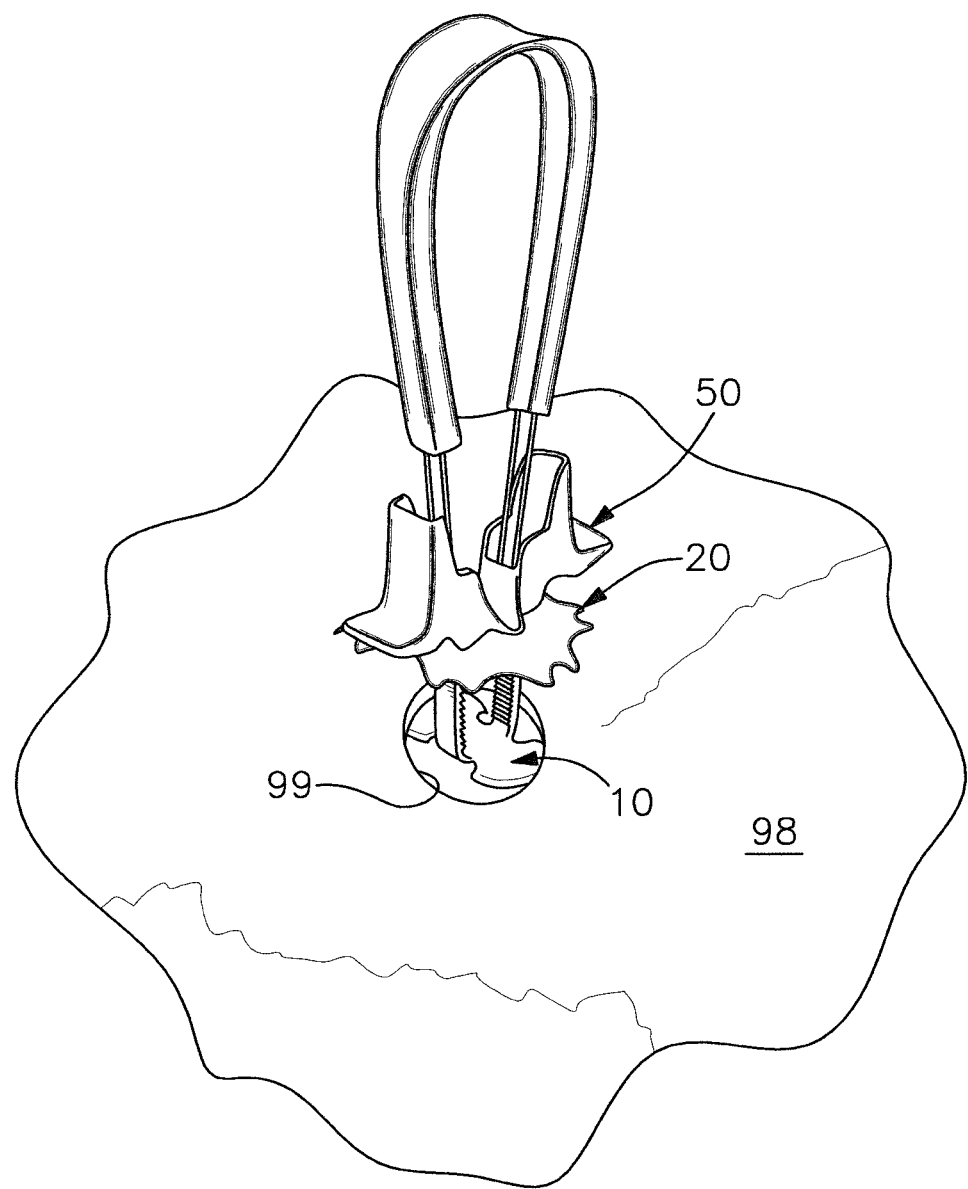
FIG. 8 illustrates the internal bracing member of the embodiment of FIG. 6 fully inserted into the burr hole and centered.

With this structure the interior bracing member 10 of the burr hole cover may be inserted through the circular burr hole 99 by holding the one or more connecting members 30 and tilting the internal bracing member 10 such that a longitudinal end 13 of the internal bracing member 10 is able to be inserted, at an angle between parallel and perpendicular to the surface of the skull 98 at the burr hole 99, i.e., the imaginary plane substantially containing the edges of the burr hole, into the burr hole 99 and under the skull 98 adjacent the burr hole 99, as shown in FIG. 7. The internal bracing member 10 is then moved laterally relative to the burr hole 99 to bring the connecting members 30 sufficiently close to the edge of the burr hole 99 to allow the opposite end 13 of the internal bracing member 10 to clear the opposite edge of the burr hole 99. This is possible because the width dimension 12 and the clearance distance 15 of the internal bracing member 10 are both smaller than the diameter of the burr hole 99. The internal bracing member 10 is then leveled relative to the skull 98 and moved laterally in the opposite direction to center the internal bracing member 10 beneath the burr hole 99 with both longitudinal ends 13 and the entire internal bracing member 10 now positioned beneath or distal to the burr hole 99 and skull 98, as shown in FIG. 8. The planar or substantially planar configuration of the internal bracing member 10 minimizes damage to internal tissue located adjacent the burr hole 99 during the positioning steps, and presents a thin, minimally-intrusive profile beneath the skull 98 once fully implanted.

Figure 9:
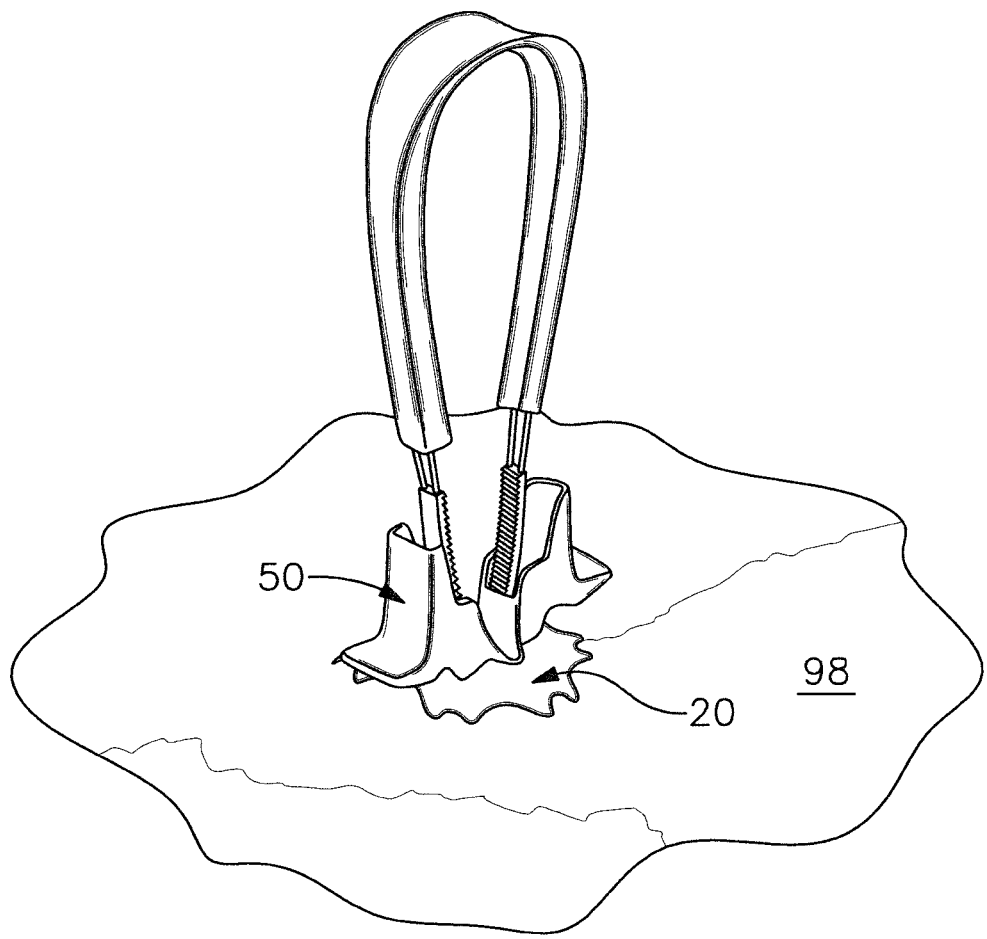
FIG. 9 shows the external cover member of the embodiment of FIG. 6 moved distally along the connecting members and in contact with the skull.
Figure 10:
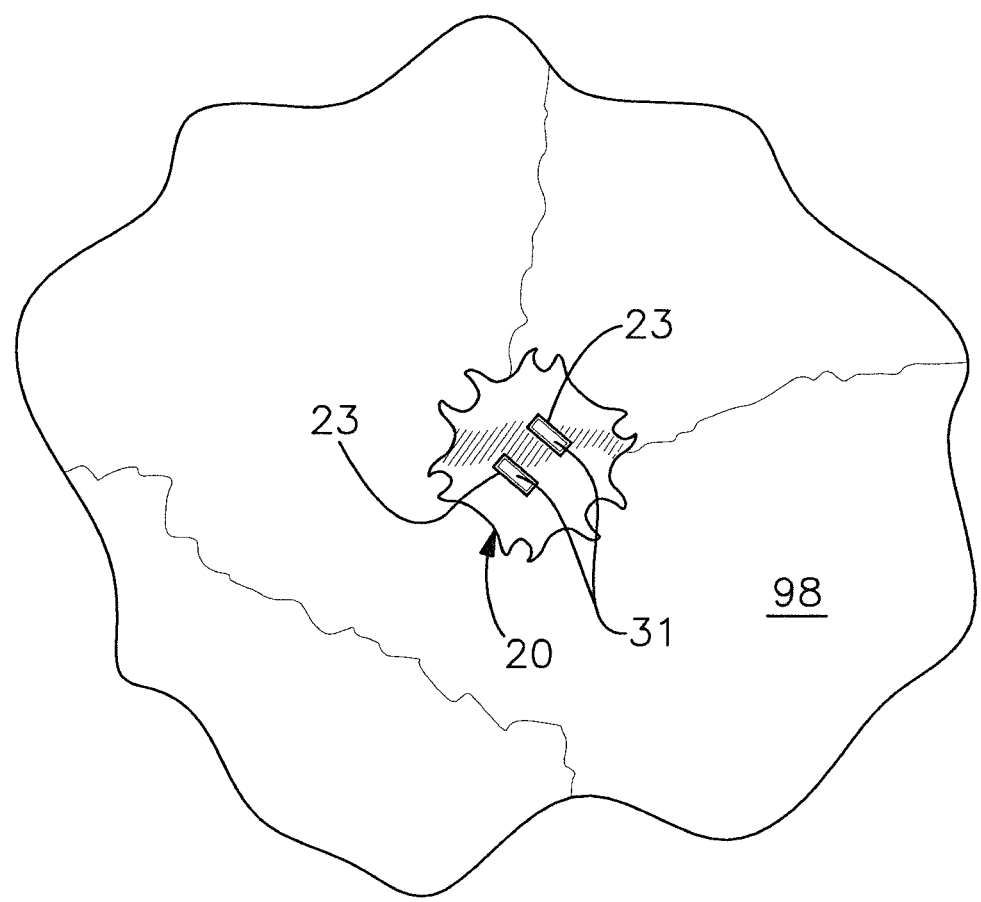
FIG. 10 shows the cranial burr hole cover of the embodiment of FIG. 6 secured onto the skull and covering the burr hole, the connecting members having been removed flush with the external cover member.

The external cover member 20 is now manually moved distally toward the skull 98 and the internal bracing member 10 to sandwich the area of the skull 98 surrounding the burr hole 99 tightly between the internal bracing member 10 and the external cover member 20, thereby fully covering the burr hole 99, as shown in FIG. 9. When the looping handle 32 is present on the connecting members 30, the surgeon will grasp the looping handle 32 with one hand or finger and push down on the actuator member 50, if present, and/or the external cover member with the other hand or fingers. The locking mechanism 40 secures the external cover member 20 in place on the skull 98 over the burr hole 99. Once secured, the portions of the connecting members 30 extending from the cover member 20 are removed, such as by cutting or breaking off flush with the cover member 20, as shown in FIG. 10.

It is contemplated that equivalents and substitutions for certain elements, structures and steps described above may be obvious to those of skill in the art, and therefore the true scope and definition of the invention is to be as set forth in the following claims.

We claim:

1. A method of covering an isolated, circular burr hole in a skull, said burr hole having a diameter and said skull having a surface and a distal side, comprising the steps of:
   measuring the diameter of the burr hole to be covered;
   providing a cranial burr hole cover device comprising a single, elongated, internal bracing member, a disk-shaped, external cover member having a diameter, one or more connecting members joining said external cover member to said internal bracing member, and a locking mechanism whereby movement of said external cover member along said connecting members toward said internal bracing member is allowed and movement of said external cover member along said connecting members away from said internal bracing member is precluded;
   said internal bracing member being planar or substantially planar and having a longitudinal dimension, a longitudinal midpoint or midline, and a maximum width dimension, said longitudinal dimension being greater than said maximum width dimension, such that said internal bracing member comprises a pair of longitudinal ends;
   said one or more connecting members joined to said internal bracing member at said midpoint or midline, whereby a clearance distance is defined extending from one of said longitudinal ends to a side of said one or more connecting members opposite from said one of said longitudinal ends;
   choosing said cranial burr hole cover device such that the diameter of said external cover member is greater than the diameter of the burr hole, such that said longitudinal dimension of said internal bracing member is greater than the diameter of the burr hole and said maximum width dimension of said internal bracing member is smaller than the diameter of the burr hole, and such that said clearance distance is smaller than the diameter of the burr hole;
   inserting one of said longitudinal ends of said internal bracing member, at an angle between perpendicular and parallel to the surface of the skull at the burr hole, through the burr hole and under the skull adjacent the burr hole;
   moving said internal bracing member laterally and inserting and leveling the other of said longitudinal ends of said internal bracing member through the burr hole, then centering said internal bracing member relative to the burr hole such that said internal bracing member is positioned entirely on the distal side of the skull and burr hole;
   securing said internal bracing member and said external cover member to the skull by moving said external cover member distally along said connecting members toward said burr hole; and
   removing portions of said connecting members that are extending proximally from said external cover member.

2. The method of claim 1, wherein said step of providing a cranial burr hole cover device further comprises providing a cranial burr hole cover device having two connecting members, each of said two connecting members having a distal end, the distal ends of said two connecting members being joined to said internal bracing member in fixed manner defining a distance between said distal ends that is not variable.

3. The method of claim 2, wherein said connecting members comprise a looped handle, and further comprising the step of grasping said looped handle with one hand or finger prior to said step of moving said external cover member distally along said connecting members toward said burr hole.

4. The method of claim 2, wherein said burr hole cover device further comprises an actuator member mounted onto said connecting members, and wherein said step of moving said external cover member distally along said connecting members toward said burr hole is accomplished by pressing against said actuator member.

5. The method of claim 1, wherein said burr hole cover device further comprises an actuator member mounted onto said one or more connecting members, and wherein said step of moving said external cover member distally along said connecting members toward said burr hole is accomplished by pressing against said actuator member.

6. The method of claim 1, wherein said portions of said connecting members that are extending proximally from said external cover member are removed by cutting.

7. The method of claim 1, wherein said portions of said connecting members that are extending proximally from said external cover member are removed by breaking.

* * * * *